United States Patent
Ishii et al.

(10) Patent No.: US 10,243,317 B2
(45) Date of Patent: Mar. 26, 2019

(54) LASER DEVICE AND PHOTOACOUSTIC MEASUREMENT DEVICE

(71) Applicant: FUJIFILM Corporation, Tokyo (JP)

(72) Inventors: Hiroyasu Ishii, Ashigarakami-gun (JP); Takatsugu Wada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 348 days.

(21) Appl. No.: 15/095,567

(22) Filed: Apr. 11, 2016

(65) Prior Publication Data

US 2016/0226214 A1    Aug. 4, 2016

Related U.S. Application Data

(63) Continuation of application No. PCT/JP2014/078448, filed on Oct. 27, 2014.

(30) Foreign Application Priority Data

Oct. 31, 2013  (JP) .................. 2013-226247
Oct. 23, 2014  (JP) .................. 2014-216083

(51) Int. Cl.
*H01S 3/115*    (2006.01)
*A61B 5/00*     (2006.01)
(Continued)

(52) U.S. Cl.
CPC ............ *H01S 3/115* (2013.01); *A61B 5/0095* (2013.01); *H01S 3/0623* (2013.01);
(Continued)

(58) Field of Classification Search
CPC ........ H01S 3/115; H01S 3/107; H01S 3/0623; H01S 3/08054; H01S 3/1633;
(Continued)

(56) References Cited

U.S. PATENT DOCUMENTS 4,837,769 A * 6/1989 Chandra ................. F41G 3/145
                                                   372/41
4,882,235 A   11/1989 Resler
(Continued)

FOREIGN PATENT DOCUMENTS

CN   102389321 A   3/2012
JP   55-56678 A    4/1980
(Continued)

OTHER PUBLICATIONS

Japanese Office Action, dated Sep. 27, 2016, for Japanese Application No. 2014-216083, together with an English translation thereof.
(Continued)

*Primary Examiner* — Xinning (Tom) Niu
(74) *Attorney, Agent, or Firm* — Birch, Stewart, Kolasch & Birch, LLP (57) ABSTRACT

Disclosed are a laser device which uses alexandrite crystal and is capable of suppressing abnormal oscillation even if the size thereof is reduced and suppressing damage to an AR coating on a Q switch or alexandrite crystal, and a photoacoustic measurement device. A laser rod 11 includes alexandrite crystal. A flash lamp 12 irradiates the laser rod 11 with excitation light. A resonator includes a pair of mirrors 14 and 15 with the laser rod 11 sandwiched therebetween. A Q switch 16 is inserted into the optical path of the resonator and controls the Q value of the resonator. A polarizer 17 is inserted into the resonator and is a non-coated Brewster polarizer which selectively transmits light in a predetermined polarization direction among light emitted from the laser rod.

17 Claims, 7 Drawing Sheets

(51) Int. Cl.

| | |
|---|---|
| *H01S 3/092* | (2006.01) |
| *H01S 3/06* | (2006.01) |
| *H01S 3/08* | (2006.01) |
| *H01S 3/16* | (2006.01) |
| *H01S 3/107* | (2006.01) |
| *H01S 3/04* | (2006.01) |
| *H01S 3/042* | (2006.01) |
| *H01S 3/10* | (2006.01) |

(52) U.S. Cl.
CPC .......... *H01S 3/08054* (2013.01); *H01S 3/092* (2013.01); *H01S 3/107* (2013.01); *H01S 3/1633* (2013.01); *H01S 3/042* (2013.01); *H01S 3/0407* (2013.01); *H01S 3/10061* (2013.01); *H01S 2301/06* (2013.01)

(58) Field of Classification Search
CPC .... H01S 3/092; H01S 3/10061; H01S 3/0407; H01S 3/042; H01S 2301/06; A61B 5/0095
See application file for complete search history.

(56) References Cited

U.S. PATENT DOCUMENTS

| | | | |
|---|---|---|---|
| 5,204,867 A * | 4/1993 | Koschmann | H01S 3/136 372/10 |
| 5,617,435 A | 4/1997 | Nagai et al. | |
| 9,153,931 B2 * | 10/2015 | Ichihara | H01S 3/082 |
| 2007/0015978 A1 * | 1/2007 | Kanayama | A61B 5/0095 600/310 |
| 2008/0069157 A1 | 3/2008 | Ariga et al. | |
| 2009/0201957 A1 * | 8/2009 | Brotherton-Ratcliffe | H01S 3/139 372/29.022 |
| 2009/0237661 A1 | 9/2009 | Yamazoe | |
| 2010/0272132 A1 | 10/2010 | Yamazoe | |
| 2014/0126591 A1 | 5/2014 | Kajiyama et al. | |
| 2014/0185634 A1 | 7/2014 | Ichihara et al. | |

FOREIGN PATENT DOCUMENTS

| | | |
|---|---|---|
| JP | 59-104558 | 7/1984 |
| JP | 2-7022 A | 1/1990 |
| JP | 5-206560 A | 8/1993 |
| JP | 7-318996 A | 12/1995 |
| JP | 2001-230479 A | 8/2001 |
| JP | 2008-85292 A | 4/2008 |
| JP | 2009-218232 A | 9/2009 |
| JP | 2009-231483 A | 10/2009 |
| JP | 2010-258198 A | 11/2010 |
| JP | 2013-74180 A | 4/2013 |
| JP | 2013-89680 A | 5/2013 |
| JP | 2013-111432 A | 6/2013 |
| WO | WO 2013/008772 A1 | 1/2013 |

OTHER PUBLICATIONS

English Translation of International Preliminary Report on Patentability (IPRP) for PCT/JP2014/078448 (including PCT/IB/326; PCT/IB/373 and PCT/ISA/237), dated May 3, 2016.
International Search Report for PCT/JP2014/078448 (PCT/ISA/210) dated Dec. 22, 2014.
Written Opinion of the International Searching Authority for PCT/JP2014/078448 (PCT/ISA/237) dated Dec. 22, 2014.
Extended European Search Report, dated Oct. 20, 2016, for corresponding European Application No. 14858991.4.
Japanese Office Action and English translation thereof, dated Apr. 4, 2017, for corresponding Japanese Application No. 2014-216083.
Chinese Official communication dated Apr. 2, 2018 in corresponding Chinese Patent Application No. 201480059016.8.
Chinese Office Action for corresponding Chinese Application No. 201480059016.8, dated Nov. 7, 2018, with English translation.
European Office Action for corresponding European Application No. 14858991.4, dated Nov. 28, 2018.

\* cited by examiner

FIG. 1

FIG. 2A distance = 200mm

FIG. 2B distance = 600mm

FIG. 3A distance = 200mm

FIG. 3B distance = 600mm

LASER DEVICE AND PHOTOACOUSTIC MEASUREMENT DEVICE

CROSS-REFERENCE TO RELATED APPLICATIONS

This application is a Continuation of PCT International Application No. PCT/JP2014/078448 filed on Oct. 27, 2014, which claims priority under 35 U.S.C. § 119(a) to Japanese Patent Application No. 2013-226247 filed on Oct. 31, 2013 and Japanese Patent Application No. 2014-216083 filed on Oct. 23, 2014. Each of the above application(s) is hereby expressly incorporated by reference, in its entirety, into the present application.

BACKGROUND OF THE INVENTION

1. Field of the Invention

The present invention relates to a laser device, and in particular, relates to a laser device which has a laser rod including alexandrite crystal and performs Q switch pulse oscillation. The present invention also relates to a photoacoustic measurement device including such a laser device.

2. Description of the Related Art

As one image inspection method which can noninvasively inspect a state inside a living body, an ultrasonography method is known. In ultrasonography, an ultrasound probe which can transmit and receive an ultrasonic wave is used. If an ultrasonic wave is transmitted from the ultrasound probe to the subject (living body), the ultrasonic wave advances through the inside of the living body, and is reflected from a tissue interface. The reflected ultrasonic wave is received by the ultrasound probe, and a distance is calculated based on the time until the reflected ultrasonic wave returns to the ultrasound probe, whereby it is possible to image a status inside the living body.

Furthermore, photoacoustic imaging which images the inside of a living body using a photoacoustic effect is known. In general, in photoacoustic imaging, the inside of the living body is irradiated with a pulse laser beam, such as a laser pulse. Inside the living body, a living body tissue absorbs the energy of the pulse laser beam, and an ultrasonic wave (photoacoustic signal) is generated due to adiabatic expansion caused by energy. The photoacoustic signal is detected by an ultrasound probe or the like, and a photoacoustic image is constituted based on a detection signal, whereby it is possible to visualize the inside of the living body based on the photoacoustic signal.

In a measurement of a photoacoustic wave, in many cases, it is necessary to emit a pulse laser beam with high intensity, and a solid-state laser device which performs Q switch pulse oscillation is used for a light source. The laser device has a laser rod (laser medium), and a flash lamp (excitation lamp) which excites the laser rod. The laser device has a Q switch for Q switch pulse oscillation. A laser device which can be used for a photoacoustic measurement is described in, for example, JP2013-089680A or JP2013-074180A. These documents describe an example where alexandrite crystal is used as a laser medium.

SUMMARY OF THE INVENTION

Alexandrite crystal can be suitably used for a Q switch pulse laser since a sectional area of induced emission is small and upper-level lifetime is comparatively long. However, alexandrite crystal is a kind of precious stone and is very expensive. Accordingly, in order to manufacture an alexandrite laser at low cost, reduction in volume of alexandrite crystal is required.

In a case where alexandrite crystal is reduced in volume, in order to obtain sufficient output (for example, equal to or greater than 100 mJ) and a sufficient pulse length (for example, equal to or less than about 100 nanoseconds) for photoacoustics with Q switch oscillation, it is necessary to increase the reflectance of an output mirror to be equal to or greater than about 70% to intensify confinement of laser. However, in this case, it has been found that light cannot be confined in a resonator until desired output, abnormal oscillation occurs, and an anti-reflection (AR) coating on the Q switch or an AR coating on the laser medium is damaged. That is, it has been found that, if an alexandrite laser is reduced in volume, it is difficult to produce Q switch oscillation with high output and a short pulse normally.

New facts have been found that, if the reflectance of the mirror is increased to intensify confinement of laser, abnormal oscillation occurs even in a situation of being confined, and damage to the AR coating on laser crystal or the AR coating on the Q switch occurs repeatedly. Such a situation causes a significant problem particularly in reliability, and the level allowable for a product is not reached.

The Q switch has temperature characteristics, and if the temperature of the Q switch changes with change in temperature of an ambient environment or change in temperature of the device, an applied voltage which confines laser (can maintain a state where laser oscillation is suppressed) changes. It is understood that, if change in temperature is great, laser cannot be confined and starts to leak from the Q switch, and abnormal oscillation with high energy density occurs at the time of leaking. Since the AR coating on the Q switch or the AR coating on alexandrite crystal is damaged due to oscillation with high energy density, this becomes a significant obstacle for producing a product.

The invention has been accomplished in consideration of the above-described situation, and an object of the invention is to provide a laser device using alexandrite crystal capable of suppressing abnormal oscillation even if the size thereof is reduced and suppressing damage to an AR coating on a Q switch or alexandrite crystal.

The invention also provides a photoacoustic measurement device including the above-described laser device.

In order to attain the above-described object, the invention provides a laser device comprising a laser rod which includes alexandrite crystal, an excitation light source which irradiates the laser rod with excitation light, a resonator which includes a pair of mirrors with the laser rod sandwiched therebetween, a Q switch which is inserted into the optical path of the resonator and controls the Q value of the resonator, and a non-coated Brewster polarizer which is inserted at least between the laser rod and the Q switch or between the laser rod and one of the pair of mirrors and selectively transmits light in a predetermined polarization direction among light emitted from the laser rod.

In the laser device of the invention, it is preferable that the optical path of the resonator is sealed within the range of the resonator.

In the laser device of the invention, at least one of the laser rod or the Q switch may have an anti-reflection film at a light incidence end thereof.

The Q switch may include a Pockels cell, when an applied voltage to the Pockels cell is a first voltage, the Q value of the resonator may be higher than a laser oscillation threshold, and when the applied voltage is a second voltage higher than the first voltage, the Q value of the resonator may be equal to or less than the laser oscillation threshold. The first voltage may be, for example, 0 V (no voltage is applied), and the second voltage may be, for example, a voltage which makes the Pockels cell function as a quarter-wave plate.

In the invention, it is preferable that, when input energy is 20 J, the range of an applied voltage to the Q switch for making the Q value of the resonator equal to or less than the laser oscillation threshold is equal to or greater than 0.5 kV.

In a preferred aspect of the invention, the polarizer is constituted of a glass plate disposed at a Brewster angle with respect to the optical axis of light emitted from the laser rod.

In the invention, it is preferable that, when input energy is 20 J, the output energy of laser is equal to or greater than 140 mJ.

In the laser device of the invention, the polarizer may be inserted between the laser rod and the output-side mirror of the pair of mirrors. Alternatively, the polarizers may be inserted both between the laser rod and the Q switch and between the laser rod and one of the pair of mirrors.

The invention also provides a laser device comprising a laser rod which includes alexandrite crystal, an excitation light source which irradiates the laser rod with excitation light, a resonator which includes a pair of mirrors with the laser rod sandwiched therebetween, a Q switch which is inserted into the optical path of the resonator and controls the Q value of the resonator, and a Brewster polarizer which is inserted at least between the laser rod and the Q switch or between the laser rod and one of the pair of mirrors, selectively transmits light in a predetermined polarization direction among light emitted from the laser rod, and has a film for separating light in the predetermined polarization direction from light in a polarization direction orthogonal to the predetermined polarization direction.

In the above description, the Q switch may include a Pockels cell, when an applied voltage to the Pockels cell is a first voltage, the Q value of the resonator may be higher than a laser oscillation threshold, and when the applied voltage is a second voltage higher than the first voltage, the Q value of the resonator may be equal to or less than the laser oscillation threshold.

In the laser device, it is preferable that, when input energy is 20 J, the range of an applied voltage to the Q switch for making the Q value of the resonator equal to or less than the laser oscillation threshold is equal to or greater than 2.5 kV.

In the laser device, it is preferable that, when input energy is 20 J, the output energy of laser is equal to or greater than 140 mJ.

The invention also provides a photoacoustic measurement device comprising the laser device of the invention, photoacoustic detection unit for detecting a photoacoustic wave generated in a subject after the subject is irradiated with a laser beam emitted from the laser device, and signal processing unit for performing signal processing based on the detected photoacoustic wave.

The laser device of the invention has the Brewster polarizer in the resonator. In a laser device using alexandrite crystal, if the laser rod including alexandrite is reduced in volume for reduction in cost, abnormal oscillation is likely to occur, and the AR coating on the Q switch or the AR coating on alexandrite crystal may be damaged. The Brewster polarizer is provided in the resonator, whereby it is possible to suppress abnormal oscillation even if the laser rod is reduced in volume and to suppress damage to the AR coating on the Q switch or alexandrite crystal.

DESCRIPTION OF THE PREFERRED EMBODIMENTS

Figure 1:
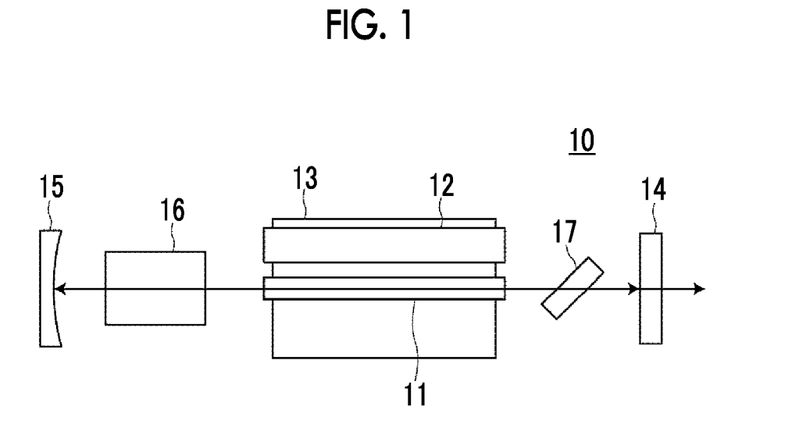
FIG. 1 is a block diagram showing a laser device of a first embodiment of the invention.

Hereinafter, an embodiment of the invention will be described in detail referring to the drawings. FIG. 1 shows a laser device of a first embodiment of the invention. A laser device 10 has a laser rod 11, a flash lamp 12, a laser chamber 13, mirrors 14 and 15, a Q switch 16, and a polarizer 17. The laser rod 11 is a laser medium. For the laser rod 11, alexandrite crystal formed in a rod shape is used. An anti-reflection coating (AR coating) is applied to an end portion (light incidence surface) of the laser rod 11. That is, the laser rod 11 has an anti-reflection film at a light incidence end thereof.

The flash lamp 12 is an excitation light source, and emits excitation light for exciting the laser rod 11. The laser rod 11 and the flash lamp 12 are housed in the laser chamber 13. The laser chamber 13 has a space for housing the laser rod 11 and the flash lamp 12 therein. A reflective surface is formed on the inner side of the laser chamber 13, and the laser rod 11 is irradiated directly with light emitted from the flash lamp 12 or the laser rod 11 is irradiated with light reflected from the reflective surface. The inner side of the laser chamber 13 may be a diffuse reflective surface.

The mirrors 14 and 15 face each other with the laser rod 11 sandwiched therebetween, and a resonator is constituted of the mirrors 14 and 15. The optical path in the optical resonator is not necessarily linear, and a prism or the like may be provided between the mirrors 14 and 15 to bend the optical path. The mirror 14 is an output coupler (OC), and the mirror 15 is a total reflection mirror. The reflectance of the mirror 14 is preferably equal to or greater than 70%. A laser beam as output light is emitted from the mirror 14.

The Q switch 16 for controlling the Q value of the resonator is inserted on the optical path of the resonator. In FIG. 1, the Q switch 16 is disposed on the optical path of light induced and emitted from the laser rod 11 between the laser rod 11 and the mirror 15. The Q switch 16 changes the polarization state of light to be transmitted therethrough according to an applied voltage. For the Q switch 16, for example, a Pockels cell is used. Similarly to the laser rod 11, an AR coating is applied to a side surface constituting the light incident surface of the Q switch 16. Specifically, an AR coating is applied to glass which covers the Pockels cell of the Q switch 16. That is, the Q switch 16 has an anti-reflection film at a light incidence end thereof.

The Q value of the resonator is controlled by changing the applied voltage to the Q switch 16. The Q switch 16 places the resonator in a high Q state when the applied voltage is a first voltage corresponding to Q switch on. The high Q state indicates a state in which the Q value of the resonator is higher than a laser oscillation threshold. The first voltage is, for example, 0 V (no voltage is applied), and at this time, the polarization state of light transmitted through the Q switch 16 is not changed. The Q switch 16 places the resonator in a low Q state when the applied voltage is a second voltage corresponding to Q switch off. The low Q state indicates a state in which the Q value of the resonator is lower than the laser oscillation threshold. The second voltage is, for example, a voltage which makes the Q switch 16 function as a quarter-wave plate, and is, for example, 2 kV.

Linearly polarized light in a predetermined polarization direction is incident on the Q switch 16 from the laser rod 11 side. When the applied voltage to the Q switch 16 is 0 V (first voltage), linearly polarized light incident on the Q switch 16 is incident on the mirror 15 without change in the polarization state, is reflected from the mirror 15, and is incident on the Q switch 16 in an opposite direction. Light passes through the Q switch 16 without change in the polarization state and is returned to the laser rod 11. In this case, the Q value of the resonator is high, and laser oscillation occurs.

When the applied voltage to the Q switch 16 is the second voltage, the Q switch 16 functions as a quarter-wave plate, and linearly polarized light incident on the Q switch 16 from the laser rod 11 side is circularly polarized when passing through the Q switch 16, is incident on the mirror 15, is reflected from the mirror 15, and is incident on the Q switch 16 in an opposite direction. Light is turned from circularly polarized light to linearly polarized light when passing through the Q switch 16, and is returned to the laser rod 11. The polarization direction of linearly polarized light having passed through the Q switch 16 in an opposite direction of the outward path is different from the polarization direction of the outward path at 90°. In this case, the Q value of the resonator is low, and laser oscillation does not occur.

Control means (drive means) (not shown) turns on the flash lamp 12 in a state where the applied voltage to the Q switch 16 is the second voltage. After the flash lamp 12 is turned on, when the population inversion density in the laser rod 11 is sufficiently high, the applied voltage to the Q switch 16 is changed from the second voltage to the first voltage. The Q value of the resonator is rapidly changed from the low Q state to the high Q state, whereby a giant pulse is obtained. The output energy of laser of a pulse laser beam output from the resonator is preferably equal to or greater than 100 mJ, and more preferably, equal to or greater than 140 mJ. The pulse time width of the pulse laser beam is preferably equal to or less than 100 nanoseconds, and more preferably, equal to or less than 60 nanoseconds.

In the above description, although the application of the first voltage corresponds to Q switch on and the application of the second voltage corresponds to Q switch off, the relationship between the on/off of the Q switch and the applied voltage may be reversed. That is, the applied voltage to the Q switch 16 being a voltage (second voltage) which makes the Q switch 16 function as a quarter-wave plate may correspond to Q switch on, and the applied voltage to the Q switch 16 being 0 V (first voltage) may correspond to Q switch off. In this case, a quarter-wave plate may be inserted between the Q switch 16 and the mirror 15.

In order to manufacture a laser device at low cost, it is preferable to reduce the volume of expensive alexandrite crystal as small as possible. However, it has been understood that, if alexandrite crystal is reduced in volume, the energy density is very high, abnormal oscillation is likely to occur when obtaining a pulse laser beam having a short pulse time width with high output, and the AR coating on the laser rod 11 or the Q switch 16 is damaged due to abnormal oscillation. Accordingly, it is difficult to stably use a laser device over a long period of time.

In a laser using alexandrite crystal, since alexandrite crystal has anisotropy and alexandrite crystal itself serves as a polarizer, primarily, it is not necessary to introduce a polarizer in the resonator. However, the inventors have found that, if a polarizer is introduced in the resonator, even in a case of using alexandrite crystal of small volume and obtaining a pulse laser beam having a short pulse time width with high output, it is possible to suppress abnormal oscillation and to stably use a laser device over a long period of time.

The polarizer 17 is inserted between the laser rod 11 and the output-side mirror 14 in the resonator. The polarizer 17 has a non-coated glass plate of a material, such as quartz glass or borosilicate glass, disposed at a Brewster angle, and selectively transmits light in a predetermined polarization direction among light emitted from the laser rod 11. In quartz glass and borosilicate glass, quartz glass has high transmittance of laser and is suitably used. Alternatively, the polarizer 17 may be inserted between the laser rod 11 and the Q switch 16. The polarizers 17 may be inserted on both sides.

The type of a polarizer which is inserted in the resonator will be considered. A dichromatic (selective absorption type) polarizer is unavailable since an organic material does not withstand laser of a high energy density. A birefringent polarizer has a discontinuous boundary since two kinds of birefringent crystal are combined, and is unavailable since the boundary surface is damaged by a laser beam of a high energy density. A polarizer which is available in this embodiment is a reflection scattering Brewster polarizer. In particular, a non-coated glass plate can be suitably used since there is no element which is damaged by light of a high energy density. The term "non-coated" means that at least a film, which is likely to be damaged by light of a high energy density, such as a film for separating light in a predetermined polarization direction from light in a polarization direction orthogonal to the predetermined polarization direction, an anti-reflection film, or a protective film, is not provided, and it is not necessary that all films are not provided.

In this embodiment, the Brewster polarizer 17 is used, whereby it is possible to suppress abnormal oscillation even in a case of obtaining a laser beam having a short pulse time width with high output in a laser device, in which the laser rod 11 is reduced in volume for reduction in size and low cost. The laser rod 11 has a diameter preferably equal to or less than 4 mm, and desirably, equal to or less than 3 mm. The rod length is preferably equal to or less than 70 mm, and desirably, equal to or less than 60 mm.

The input energy of laser, that is, energy which is input to the flash lamp 12 as an excitation light source at the time of excitation is preferably equal to or less than 22 J since input energy leads to cost of a power supply part which supplies power to the flash lamp 12 and significantly affects the total device cost. In order to obtain desired output and a pulse time width with such low input energy, for example, the output energy of laser equal to or greater than 100 mJ, and more preferably, equal to or greater than 150 mJ and a pulse time width equal to or less than 100 nanoseconds, and more preferably, equal to or less than 60 nanoseconds, the efficiency of output energy to input energy is equal to or greater than 0.007, and more preferably, equal to or greater than 0.008. That is, if input energy is 22 J, preferably, the output energy of laser equal to or greater than about 150 mJ is obtained, and more preferably, the output energy of laser equal to or greater than about 180 mJ is obtained.

Figure 2A:
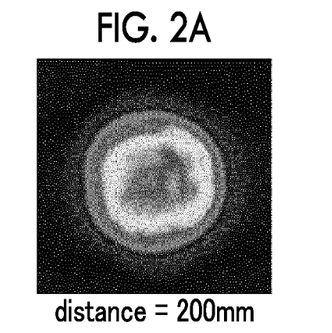
FIGS. 2A and 2B are diagrams showing a beam profile in a laser device with no polarizer.
Figure 2B:
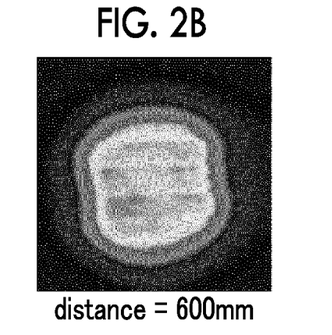

FIGS. 2A and 2B show a beam profile in a laser device with no polarizer 17. FIG. 2A shows a beam profile at a position of 200 mm from the end portion of the laser rod 11, and FIG. 2B shows a beam profile at a position of 600 mm from the end portion of the laser rod 11. In both cases, input energy is 14 J, the pulse time width is 47 nanoseconds, and the reflectance of the output-side mirror 14 is 70%. Referring to FIGS. 2A and 2B, it is understood that the energy density of the beam center portion is high in a case where the polarizer 17 is not provided.

Figure 3A:
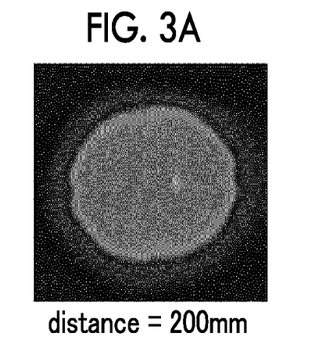
FIGS. 3A and 3B are diagrams showing a beam profile in the laser device of the first embodiment.
Figure 3B:
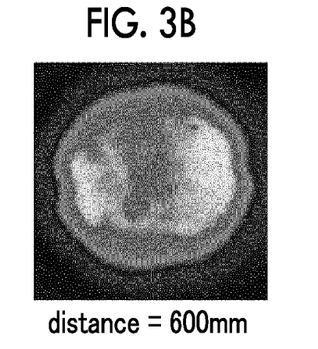

FIGS. 3A and 3B show a beam profile in a laser device with the polarizer 17. FIG. 3A shows a beam profile at a position of 200 mm from the end portion of the laser rod 11, and FIG. 3B shows a beam profile at a position of 600 mm from the end portion of the laser rod 11. In both cases, input energy is 14 J, the pulse time width is 47 nanoseconds, and the reflectance of the output-side mirror 14 is 70%. In comparison of FIGS. 3A and 3B and FIGS. 2A and 2B, it is understood that the polarizer 17 is provided to make the energy density uniform. Even in a case where the laser rod 11 is reduced in volume and the reflectance of the output-side mirror 14 is increased to intensify confinement, it is possible to suppress the occurrence of a place where the energy density is high locally; thus, it is possible to prevent abnormal oscillation and to reduce a risk of damage to the AR coating or the like.

Figure 4:
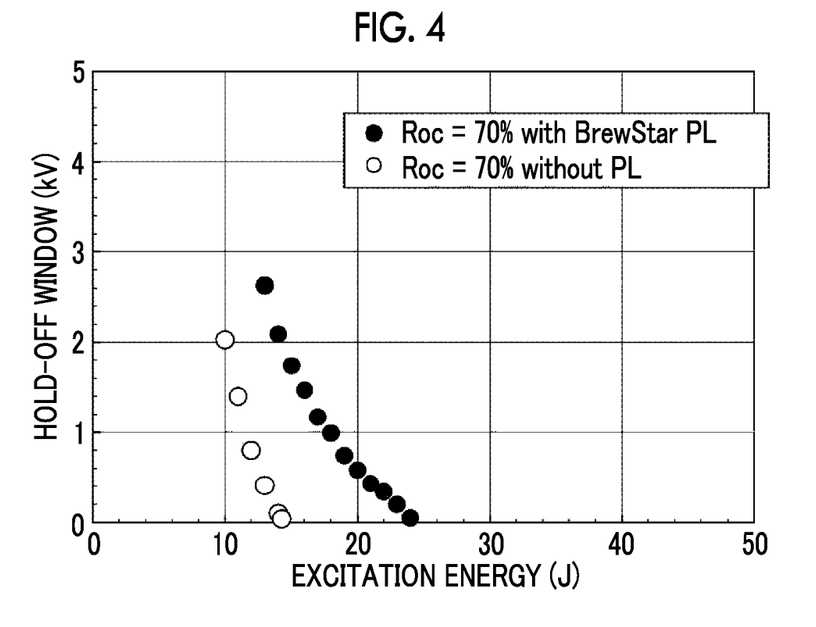
FIG. 4 is a graph showing the relationship between input energy and a voltage range in which a Q switch can be maintained off.

FIG. 4 shows the relationship between input energy and a voltage range (hold-off window) in which the Q switch 16 can be maintained off. The Q switch 16 is configured such that the applied voltage being 0 V corresponds to Q switch on, and the applied voltage being the voltage which makes the Q switch 16 function as a quarter-wave plate corresponds to Q switch off. In this drawing, the relationship (plots of black circles) between input energy and the hold-off window in a case where there is the polarizer 17 and the relationship (plots of white circles) between input energy and the hold-off window in a case where there is no polarizer 17 are shown. When the voltage range in which the Q switch 16 can be made off is narrow, it is necessary to accurately control the applied voltage of the Q switch 16 to the voltage which makes the Q switch 16 function as a quarter-wave plate, and if the voltage which makes the Q switch 16 function as a quarter-wave plate changes with change in temperature, the Q switch 16 is hardly maintained off. The width of the hold-off window is associated with a margin to change in temperature.

In comparison of a case where there is the polarizer 17 and a case where there is no polarizer 17, it is understood that the wide width of the hold-off window is obtained to the same input energy in the configuration in which there is the polarizer 17. For example, when input energy is 20 J, in the configuration in which there is the polarizer 17, it is possible to make the width of the hold-off window equal to or greater than 0.5 kV. Accordingly, in the configuration in which there is the polarizer 17, even when the voltage which makes the Q switch 16 function as a quarter-wave plate somewhat varies with change in temperature, it is possible to prevent laser from being not completely confined and leaking from the Q switch 16, and to suppress abnormal oscillation due to change in temperature. Abnormal oscillation is suppressed, whereby it is possible to prevent damage to the AR coating or the like on the laser rod 11 or the Q switch 16.

Figure 5:
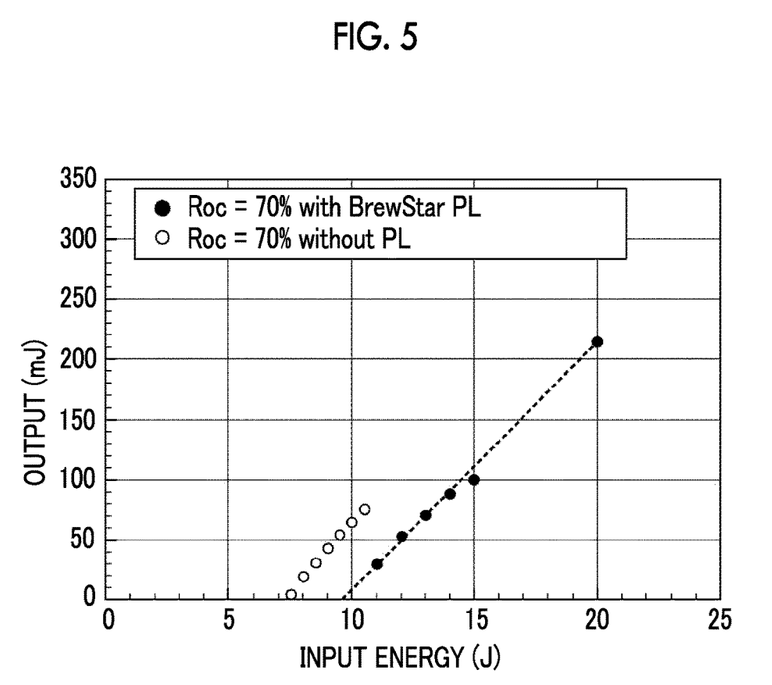
FIG. 5 is a graph showing the relationship between input energy and output energy.

FIG. 5 shows the relationship between input energy and output energy. In this case, the Q switch 16 is also configured such that the applied voltage being 0 V corresponds to Q switch on, and the applied voltage being the voltage which makes the Q switch 16 function as a quarter-wave plate corresponds to Q switch off. The output energy of laser was measured using PYRO ELECTRIC SENSOR PE25BF-C manufactured by Ophir Optronics Solutions Ltd. In this drawing, the relationship (plots of black circles) between input energy and output energy in a case where there is the polarizer 17 and the relationship (plots of white circles) between input energy and output energy in a case where there is no polarizer 17 are shown. Also referring to FIG. 4, in the configuration in which there is no polarizer 17, it is not possible to maintain the Q switch 16 off, and accordingly it is not possible to significantly increase input energy, and accordingly, it is difficult to obtain output of 150 mJ. In the configuration in which there is the polarizer 17, it is possible to input energy exceeding 20 J and to obtain output of 150 mJ.

In this embodiment, in particular, a polarizer which has a non-coated glass plate disposed at a Brewster angle is used as the polarizer 17. The non-coated glass plate can be stably used even in a laser of a high energy density without possibility of damage. The polarizer 17 is used in an alexandrite laser in which a polarizer is not required primarily, whereby there are dramatic effects of dramatically improving confinement of energy and suppressing the occurrence of abnormal oscillation. In particular, in a case where the reflectance of the output-side mirror 14 is set to 70% and confinement in the resonator is intensified, it is difficult to realize a pulse laser beam of high output and a short pulse with no polarizer 17. It is also possible to dramatically improve an allowable width to temperature, and light leakage from the Q switch 16 does not occur with change at a room-temperature level.

In this embodiment, the laser rod 11 constituted of alexandrite crystal is formed of preferably equal to or less than the rod diameter of 4 mm×the rod length of 70 mm, and more preferably, equal to or less than the rod diameter of 3 mm×the rod length of 60 mm. There is no precedent for an alexandrite laser using crystal having such small volume, and a laser device can be realized at very low cost. In a case where the laser rod 11 is reduced in volume, the rod length of the laser rod 11 is shortened, and accordingly, a component orthogonal to a predetermined polarization direction is increased. Light leakage is likely to occur due to light of the orthogonal component and abnormal oscillation is induced. In this embodiment, since light of the orthogonal component can be suppressed by the polarizer 17, it is possible to suppress the occurrence of light leakage and to suppress abnormal oscillation.

In comparison with JP2013-089680A, JP2013-089680A discloses a two-wavelength oscillation laser device, and a Brewster polarizer is used as branch means for branching an optical path for each wavelength. In contrast, in this embodiment, the Brewster polarizer 17 is provided in order to prevent damage to the AR coating on the laser rod 11 or the Q switch 16, the purpose of use of the Brewster polarizer is different apparently in JP2013-089680A and this embodiment. In JP2013-089680A, there is no description of the use of a non-coated Brewster polarizer.

In JP2013-074180A, only a configuration in which a polarizer is used as a part of a Q switch is described. In JP2013-074180A, there is no discussion that, in a laser using alexandrite crystal having small volume, abnormal oscillation occurs and an AR coating is damaged due to abnormal oscillation. In JP2013-074180A, in particular, the type of the polarizer is not limited, and there is no description that a Brewster polarizer is used, whereby it is possible to prevent damage to the AR coating on the laser rod 11 or the Q switch 16 and to stably use a laser device over a long period of time.

Next, a second embodiment of the invention will be described. A laser device of this embodiment has the same configuration as the laser device 10 of the first embodiment shown in FIG. 1. The laser device of this embodiment is different from the laser device 10 of the first embodiment in that a Brewster thin-film polarizer, that is, a Brewster polarizer having a film (separation film) for separating light in a predetermined polarization direction from light in a polarization direction orthogonal to the predetermined polarization direction, is used as the polarizer 17. Other parts may be the same as those in the first embodiment.

Figure 6:
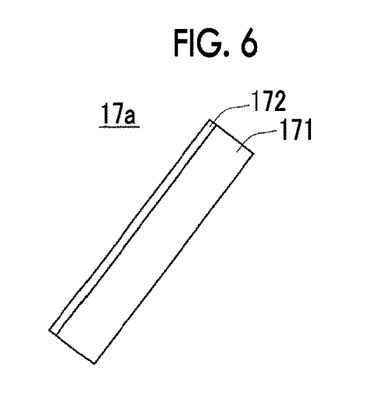
FIG. 6 is a diagram showing a polarizer for use in a laser device of a second embodiment of the invention.

FIG. 6 shows a polarizer 17a for use in this embodiment. The polarizer 17a has a glass plate 171 and a separation film 172. The glass plate 171 is a glass plate, such as quartz glass or borosilicate glass. Of quartz glass and borosilicate glass, quartz glass is suitably used since transmittance of laser is high. The separation film 172 is a film, such as a dielectric film, laminated on the glass plate 171, and is a film for separating light in a predetermined polarization direction from light in a polarization direction orthogonal to the predetermined polarization direction. Light of a component orthogonal to the predetermined direction included in light transmitted through the polarizer 17a is decreased by the separation film 172. For the polarizer 17a, for example, Product Name TP-800-B-1025 manufactured by Lattice Electro Optics Inc. is available.

Figure 7:
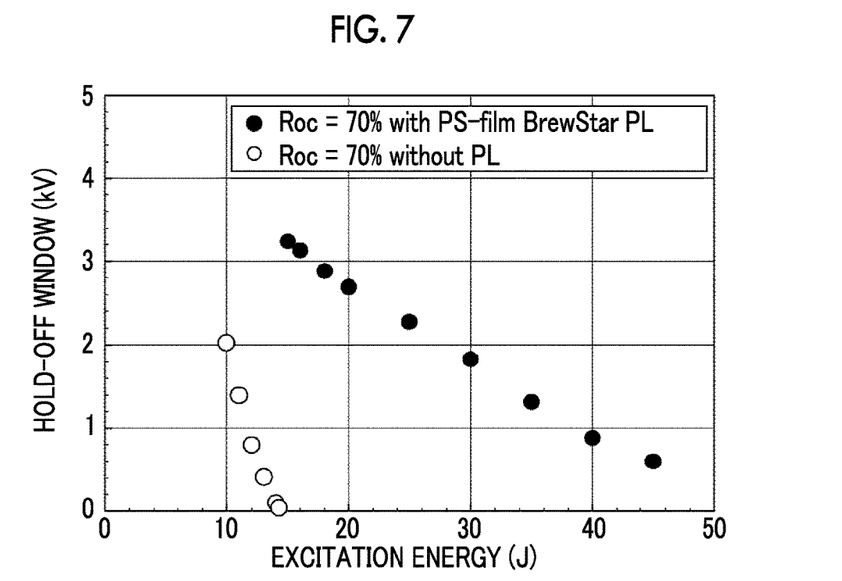
FIG. 7 is a graph showing the relationship between input energy and a voltage range, in which a Q switch can be maintained off, in the second embodiment.

FIG. 7 shows the relationship between input energy and a voltage range (hold-off window) in which the Q switch 16 can be maintained off. The Q switch 16 is configured such that the applied voltage being 0 V corresponds to Q switch on, and the applied voltage being the voltage which makes the Q switch 16 function as a quarter-wave plate corresponds to Q switch off. In this drawing, the relationship (plots of black circles) between input energy and the hold-off window in a case where there is the polarizer 17a and the relationship (plots of white circles) between input energy and the hold-off window in a case where there is no polarizer 17a are shown.

In comparison of a case where there is the polarizer 17a and a case where there is no polarizer 17a, it is understood that the considerably wide width of the hold-off window is obtained to the same input energy in the configuration in which there is the polarizer 17. For example, when input energy is 20 J, in the configuration in which there is the polarizer 17a, it is possible to make the width of the hold-off window equal to or greater than 2.5 kV. Accordingly, in the configuration in which there is the polarizer 17a, even when the voltage which makes the Q switch 16 function as a quarter-wave plate varies with change in temperature, it is possible to prevent laser from being not completely confined and leaking from the Q switch 16, and to suppress abnormal oscillation due to change in temperature. Abnormal oscillation is suppressed, whereby it is possible to prevent damage to the AR coating or the like on the laser rod 11 or the Q switch 16.

Figure 8:
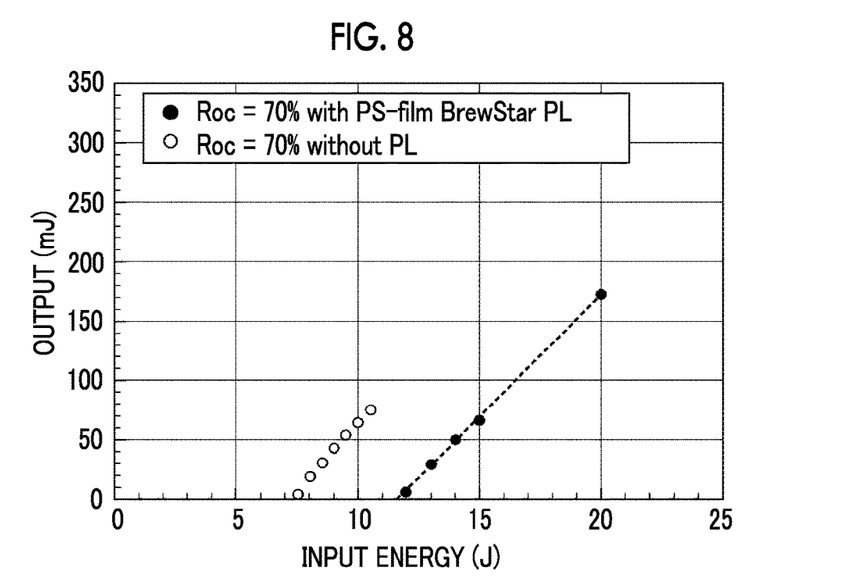
FIG. 8 is a graph showing the relationship between input energy and output energy in the second embodiment.

FIG. 8 shows the relationship between input energy and output energy. In this case, the Q switch 16 is also configured such that the applied voltage being 0 V corresponds to Q switch on and the applied voltage being the voltage which makes the Q switch 16 function as a quarter-wave plate corresponds to Q switch off. The output energy of laser was measured using PYRO ELECTRIC SENSOR PE25BF-C manufactured by Ophir Optronics Solutions Ltd. In this drawing, the relationship (plots of black circles) between input energy and output energy in a case where there is the polarizer 17a and the relationship (plots of white plots) between input energy and output energy in a case where there is no polarizer 17a are shown. Also referring to FIG. 7, in the configuration in which there is no polarizer 17a, it is not possible to maintain the Q switch 16 off, and accordingly it is not possible to significantly increase input energy, and accordingly, it is difficult to obtain output of 150 mJ. In the configuration in which there is the polarizer 17a, it is possible to input energy exceeding 20 J and to obtain output equal to or greater than 150 mJ.

In this embodiment, the Brewster polarizer 17a which has the separation film 172 for separating light in the predetermined polarization direction from light orthogonal to the predetermined polarization direction is used. As in the first embodiment, the Brewster polarizer is used, whereby it is possible to suppress abnormal oscillation to suppress damage to the AR coating on the laser rod 11 or the Q switch 16 and to improve the allowable width to temperature compared to a case where no polarizer is used.

In comparison of the first embodiment and the second embodiment, in the second embodiment, since the polarizer 17a having the separation film 172 is used, it is possible to further suppress light of the component orthogonal to the predetermined direction by the polarizer 17a and to further suppress the occurrence of light leakage in the Q switch 16 compared to the first embodiment. As will be apparent from comparison of FIGS. 4 and 7, it is possible to further improve the allowable width to temperature compared to the first embodiment.

In the second embodiment, the polarizer 17a has the separation film 172, and if the energy density is too high, the separation film 172 may be damaged. In contrast, in the first embodiment, since the non-coated Brewster polarizer is used, there is little possibility that the polarizer 17 will be damaged by light of a high energy density. While the output energy of laser may be changed according to the rotation angle between the polarizer 17a and optical parts, such as the laser rod 11, the mirrors 14 and 15, and the Q switch 16, in the second embodiment, the range of the rotation angle at which a high output energy of laser is obtained is narrower than the first embodiment. That is, the adjustment range of the rotation angle at which a high output energy of laser is obtained is narrow. In the first embodiment in which the polarizer 17 with no separation film is used, the efficiency of output energy to input energy to the flash lamp is high compared to the second embodiment in which the polarizer 17a with the separation film is used.

Figures 9, 10:
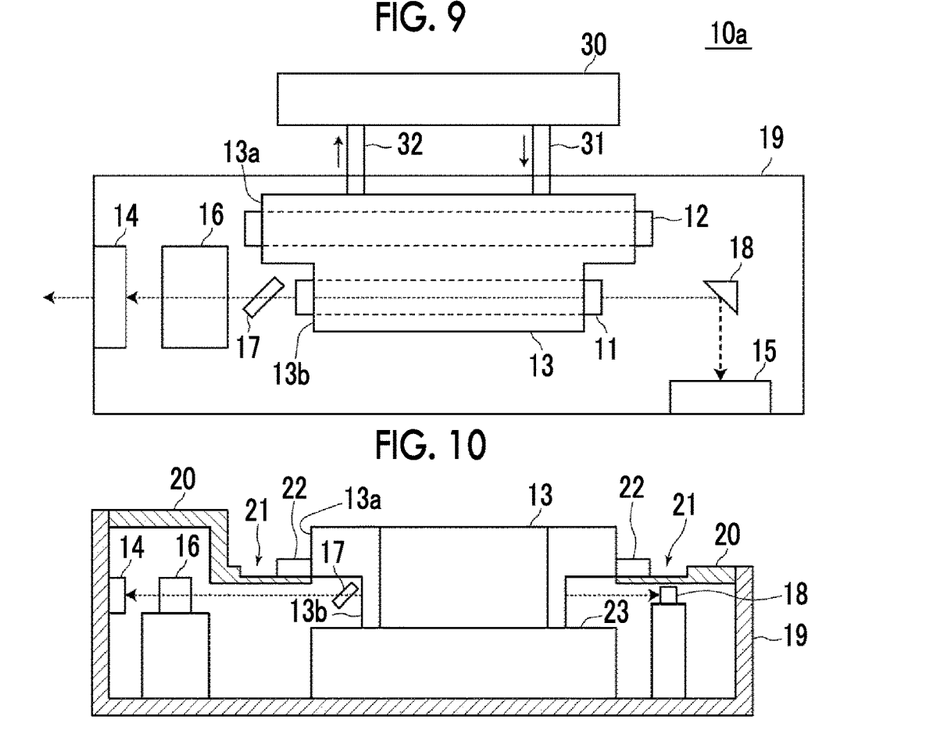
FIG. 9 is a block diagram showing a laser device according to a third embodiment of the invention.
FIG. 10 is a sectional view showing a section near the center of the laser device.

Next, a third embodiment of the invention will be described. FIG. 9 shows a laser device according to the third embodiment of the invention. A laser device 10a according to the third embodiment has a laser rod 11, a flash lamp 12, a laser chamber 13, mirrors 14 and 15, a Q switch 16, a polarizer 17, and a prism 18. The laser rod 11, the flash lamp 12, the laser chamber 13, the mirrors 14 and 15, the Q switch 16, the polarizer 17, and the prism 18 are disposed in a boxlike housing 19. Although not shown in FIG. 9, the laser device 10a has a plate-shaped shielding lid which shields the internal space of the housing 19 from the outside. FIG. 9 is also a diagram illustrating the constituent elements of the laser device 10a, and in FIG. 9, the spatial positional relationship between the constituent elements is not completely shown.

The laser rod 11, the flash lamp 12, the laser chamber 13, the mirrors 14 and 15, the Q switch 16, and the polarizer 17 may be the same as those described in the first embodiment or the second embodiment. In the laser device 10a shown in FIG. 9, the Q switch 16 is disposed on the optical path of light induced and emitted from the laser rod 11 between the laser rod 11 and the mirror 14. The polarizer 17 is disposed on the optical path of light induced and emitted from the laser rod 11 between the laser rod 11 and the Q switch 16.

In the laser device 10a shown in FIG. 9, the mirror 14 is attached to the side surface of the housing 19 in a transverse direction, and the mirror 15 is attached to the side surface of the housing 19 in a longitudinal direction orthogonal to the side surface of the transverse direction. A prism is disposed between the laser rod 11 and the mirror 15, and light emitted from the laser rod 11 is turned by the prism 18 and is directed toward the mirror 15. The prism 18 may not be provided, and the optical path in the optical resonator may be made linear.

The laser chamber 13 is connected to cooling equipment 30 through pipings 31 and 32. The cooling equipment 30 is equipment for cooling the laser rod 11 and flash lamp 12. The cooling equipment 30 feeds a cooling medium, such as pure water, into the laser chamber 13 through the piping 31. The cooling equipment 30 receives wastewater from the laser chamber 13 through the piping 32, decreases the temperature of the cooling medium, and feeds the cooling medium into the laser chamber 13 again. In this way, the cooling medium is circulated, whereby it is possible to maintain the temperature of the laser rod 11 in the laser chamber 13 in a desired temperature range.

The laser chamber 13 includes a frame body which is formed of, for example, a metal material. The laser chamber 13 has a first portion 13a which houses the flash lamp 12 and a second portion 13b which houses the laser rod 11. The first portion 13a has a hole portion having a diameter greater than the outer diameter of the flash lamp 12, and the flash lamp 12 is retractable through the hold portion in a longitudinal direction with respect to the laser chamber 13. The second portion 13b has a hole portion through which the laser rod 11 is inserted into the inside. The length of the first portion 13a in the longitudinal direction is longer than the length of the second portion 13b in the longitudinal direction. The lengths of the first portion 13a and the second portion 13b in the longitudinal direction may be the same.

In a case where alexandrite crystal for use in the laser rod 11 is reduced in volume, the flash lamp (excitation light source) 12 which emits excitation light is also reduced in size. If the excitation light source is reduced in size, the energy density per unit length of the excitation light source is increased, and the temperature is remarkably increased in the end portion of the excitation light source. It has been found that, if a shimmering phenomenon by heated air occurs in the optical path in the resonator due to an increase in temperature, the output intensity of laser fluctuates greatly. In this embodiment, in order to suppress fluctuation of the output intensity of laser, a structure in which the optical path of the resonator is sealed within the range of the resonator is used.

FIG. 10 shows a section near the center of the laser device. The mirror 14, the Q switch 16, the prism 18, and the like are attached to the housing 19. The laser chamber 13 is attached to the housing 19 through an insulating member 23. A shielding lid (shielding unit) 20 covers the housing 19 to shield the optical path of a light beam emitted from the mirror 14, the Q switch 16, the polarizer, the prism 18, and the laser rod from the outside. That is, the optical path of the resonator is sealed by the housing 19 and the shielding lid within the range of the resonator. The shielding lid 20 is formed of, for example, insulating resin, such as polycarbonate, nylon, or ABS resin.

In the laser chamber 13, the first portion 13a is exposed from the shielding lid 20. An insulating block 22 for insulating the electrode of the flash lamp 12 (see FIG. 9) is attached to the exposed first portion 13a through an O ring. The shielding lid 20 has a thin-film portion 21 having thickness smaller than the thickness of other portions of the shielding lid 20 in at least a part of a region covering the optical path of the laser beam on the outside of the first portion 13a in the longitudinal direction.

The insulating block 22 is formed of, for example, resin, such as ABS resin or acetal resin (POM). The insulating block 22 is screwed to the laser chamber 13 through the O ring in the used state of the laser device. The insulating block 22 is detached from the laser chamber 13 when replacing the flash lamp 12. The shielding lid 20 has the thin-film portion 21 in a certain range from the end portion of the first portion 13a of the laser chamber in the longitudinal direction of the laser chamber 13 centering on the optical axis of the laser beam. The thin-film portion 21 is not necessarily the same member as the shielding lid 20, and may be a separate member.

Referring to FIG. 10, in the shielding lid 20, a portion positioned below the insulating block 22 becomes the thin-film portion 21. The thickness of the thin-film portion 21 of the shielding lid 20 is, for example, 0.5 mm, and the thickness of other portions is 6 mm. If the thickness of a portion of the shielding lid 20 in contact with the end portion of the first portion 13a of the laser chamber is 6 mm which is the same as the thickness of other portions, the position of the hole portion in the insulating block 22 and the first portion 13a is moved away from the laser rod 11 (see FIG. 9) by the difference in thickness from the thin-film portion 21 compared to a case where the thin-film portion 21 is provided. If the thickness of the thin-film portion 21 is set to the normal thickness (6 mm) without moving the hole portion in the insulating block 22 and the first portion 13a, the shielding lid 20 interferes with the laser beam this time.

In a case where the first portion 13a of the laser chamber is exposed from the shielding lid 20, in particular, a portion of the end portion to which the O ring is attached is likely to interfere with the shielding lid 20. In a case where a certain range from the end portion of the first portion 13a of the laser chamber 13 having the portion of the shielding lid 20, to which the O ring is attached, is defined as the thin-film portion 21, it is possible to replace the flash lamp 12 without exposing the optical members inside the resonator, and to shorten the distance between the laser rod 11 and the flash lamp 12 compared to a case where the shielding lid 20 has a constant thickness. Therefore, it is possible to improve excitation efficiency.

If the total thickness of the shielding lid 20 is made small, the distance between the laser rod 11 and the flash lamp 12 can be narrowed. However, if the entire shielding lid 20 has the same thickness as the thin-film portion 21, the strength of the shielding lid 20 is insufficient. If the thickness of a partial region in the shielding lid 20 extending from the first portion 13a of the laser chamber 13 and covering the optical path of the laser beam is made small, it is possible to narrow the distance between the laser rod 11 and the flash lamp 12 while maintaining overall strength.

Figure 11:
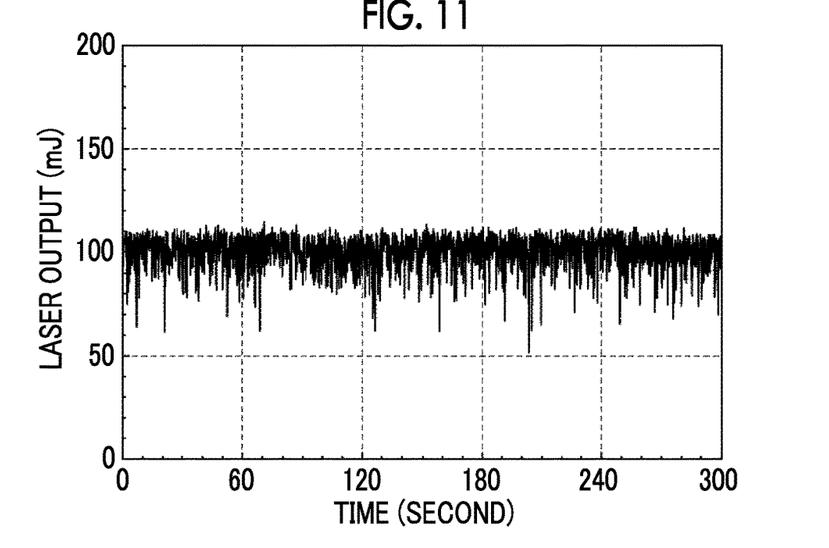
FIG. 11 is a graph showing fluctuation of the output intensity of laser in a case where an optical path of a resonator is not sealed.

FIG. 11 is a graph showing fluctuation of the output intensity of laser in a case where the optical path of the resonator is not sealed. In the graph, the vertical axis indicates the output intensity of laser, and the horizontal axis indicates time. If a pulse laser beam is emitted in a repetition period of 10 Hz, and the output intensity of each pulse laser beam is measured and plotted, the graph shown in FIG. 11 is obtained. In a case where the optical path of the resonator is not sealed and the polarizer 17 is not inserted, as shown in FIG. 11, the output intensity fluctuates greatly between the respective laser emissions, and the output intensity of laser is not stable. A mean value M of the output intensity of laser is 100 mJ, and a standard deviation σ is 7.69 mJ. If a coefficient of variation (CV) is defined as σ/M, 3CV (the ratio of 3σ to the mean value M) which is three times the coefficient of variation becomes 23.1%.

Figure 12:
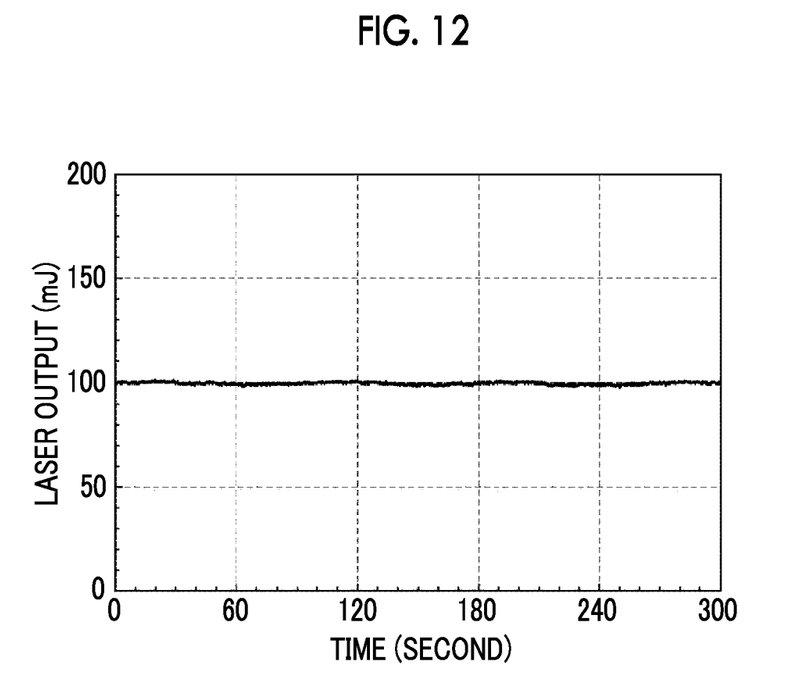
FIG. 12 is a graph showing fluctuation of the output intensity of laser in a case where the optical path of the resonator is sealed.

FIG. 12 is a graph showing fluctuation of the output intensity of laser in a case where the optical path of the resonator is sealed. In the graph, the vertical axis indicates the output intensity of laser, and the horizontal axis indicates time. A repetition period of a pulse laser beam is 10 Hz. In a case where the optical path of the resonator is sealed and the polarizer 17 is inserted, as shown in FIG. 12, the output intensity of laser is substantially constant at 100 mJ, and the output intensity of laser is stable between the respective laser emissions. The mean value M of the output intensity of laser is 100 mJ, and the standard deviation σ is 0.57 mJ. 3CV described above becomes 1.7%. When comparing with a case where the optical path is not sealed, it is understood that 3CV which is three times the coefficient of variation can be improved greatly from 23.1% to 1.7%. The reason because the output intensity of laser is stable by sealing the optical path is that, even if there is a place in the resonator where the temperature is high locally, a rapid flow of air hardly occurs, and accordingly, shimmering does not occur.

In this embodiment, a structure in which the optical path of the resonator is sealed within the range of the resonator is used. The optical path is sealed, whereby it is possible to suppress a shimmering phenomenon which is a cause of fluctuation of the output intensity of laser even when the temperature is increased in the end portion of the flash lamp 12. In this embodiment, with reduction in the volume of the laser rod 11, even in a case where the energy density per unit length of the flash lamp 12 is increased, it is possible to suppress the occurrence of shimmering and to suppress fluctuation of the output intensity of laser. In this embodiment, it should suffice that the optical path of the constituent elements of the resonator and the resonator is sealed, and the sealing structure is not particularly limited to the above-described structure.

Figure 13:
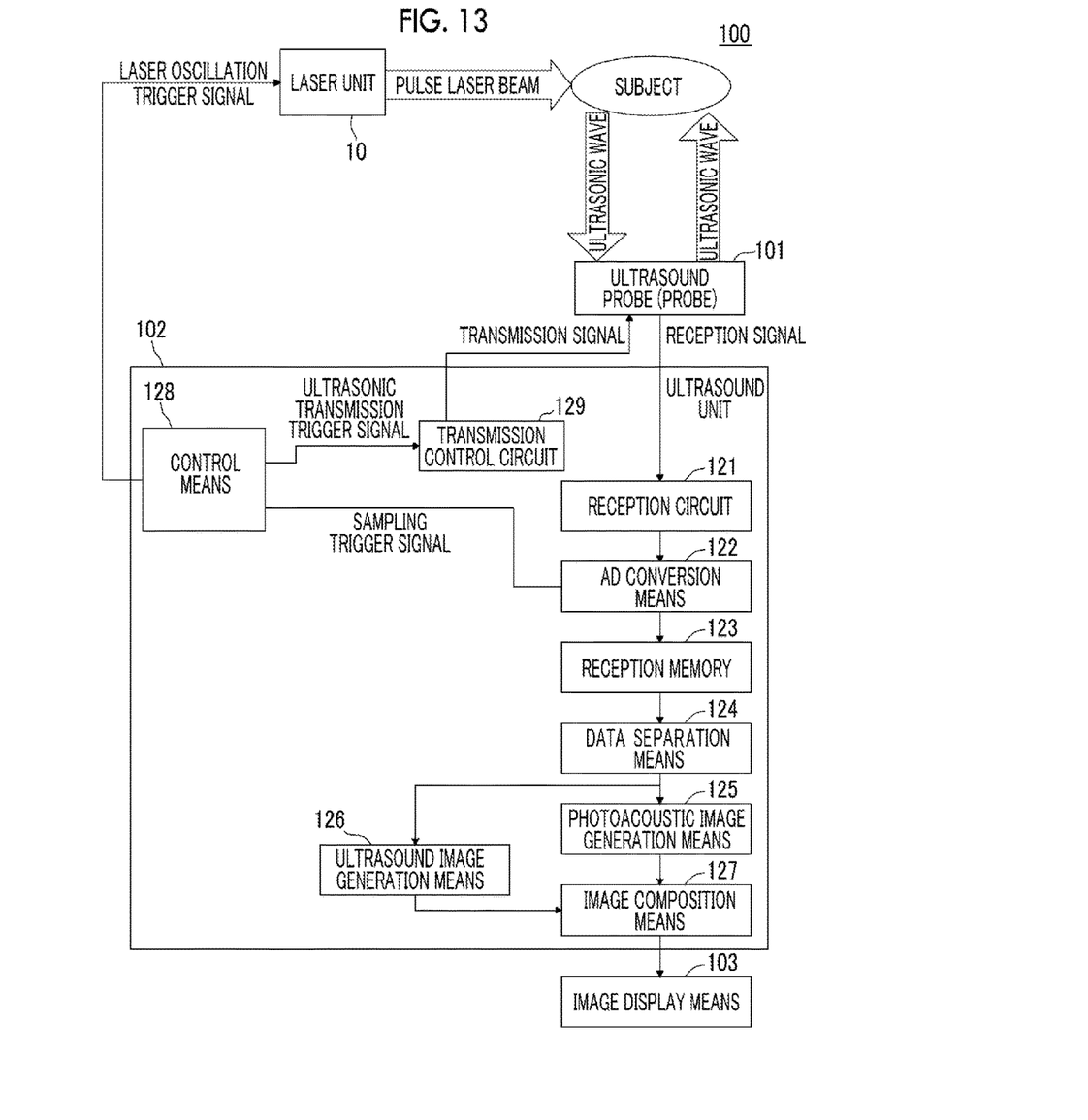
FIG. 13 is a block diagram showing a photoacoustic measurement device including the laser device of the invention.

Subsequently, a photoacoustic measurement device including the laser device of the invention will be described. FIG. 13 shows a photoacoustic measurement device including the laser device 10. A photoacoustic measurement device 100 comprises an ultrasound probe (probe) 101, an ultrasound unit 102, and a laser device (laser unit) 103. In the embodiment of the invention, although an ultrasonic wave is used as an acoustic wave, the invention is not limited to the ultrasonic wave, and an acoustic wave having an audio frequency may be used as long as an appropriate frequency has to be selected according to an inspection target, the measurement conditions, or the like.

A laser beam emitted from the laser device 10 is guided to the probe 101, for example, using light guide means, such as an optical fiber, and is irradiated from the probe 101 toward a subject. The irradiation position of the laser beam is not particularly limited, and the irradiation of the laser beam may be performed from a place other than the probe 101.

Inside the subject, an optical absorber absorbs the energy of the irradiated laser beam, and thus, an ultrasonic wave (photoacoustic wave) is generated. The probe 101 is acoustic wave detection unit, and has, for example, a plurality of ultrasonic vibrators arranged in a one-dimensional manner. The probe 101 detects an acoustic wave (photoacoustic wave) from the inside of the subject by a plurality of ultrasonic vibrators arranged in a one-dimensional manner. The probe 101 transmits an acoustic wave (ultrasonic wave) to the subject and receives a reflected acoustic wave (reflected ultrasonic wave) of the transmitted ultrasonic wave from the subject.

The ultrasound unit 102 is signal processing unit, and has a reception circuit 121, AD conversion means 122, a reception memory 123, data separation means 124, photoacoustic image generation means 125, ultrasound image generation means 126, image composition means 127, control means 128, and a transmission control circuit 129. The reception circuit 121 receives a detection signal of the photoacoustic wave detected by the probe 101. The reception circuit 121 also receives a detection signal of the reflected ultrasonic wave detected by the probe 101. The AD conversion means 122 converts the detection signals of the photoacoustic wave and the reflected ultrasonic wave received by the reception circuit 121 to digital signals. The AD conversion means 122 samples the detection signals of the photoacoustic wave and the reflected ultrasonic wave in a predetermined sampling period, for example, based on a sampling clock signal having a predetermined period. The AD conversion means 122 stores the sampled detection signals (sampling data) of the photoacoustic wave and the reflected ultrasonic wave in the reception memory 123.

The data separation means 124 separates sampling data of the detection signal of the photoacoustic wave stored in the reception memory 123 from sampling data of the detection signal of the reflected ultrasonic wave. The data separation means 124 inputs sampling data of the detection signal of the photoacoustic wave to the photoacoustic image generation means 125. The data separation means 124 also inputs the separated sampling data of the reflected ultrasonic wave to the ultrasound image generation means (reflected acoustic image generation means) 126.

The photoacoustic image generation means 125 generates a photoacoustic image based on the detection signal of the photoacoustic wave detected by the probe 101. The generation of the photoacoustic image includes, for example, image reconstruction, such as phase matching addition, detection, logarithmic conversion, and the like. The ultrasound image generation means 126 generates an ultrasound image (reflected acoustic image) based on the detection signal of the reflected ultrasonic wave detected by the probe 101. The generation of the ultrasound image includes image reconstruction, such as phase matching addition, detection, logarithmic conversion, and the like.

The image composition means 127 composes the photoacoustic image and the ultrasound image. For example, the image composition means 127 performs image composition by overlapping the photoacoustic image and the ultrasound image. A composite image is displayed on image display means 103, such as a display. Image composition may not be performed, and the photoacoustic image and the ultrasound image may be displayed in parallel on the image display means 103, or the photoacoustic image and the ultrasound image may be switched and displayed.

The control means 128 controls the respective units in the ultrasound unit 102. For example, the control means 128 sends a trigger signal to the laser device. If the trigger signal is received, drive means (not shown) in the laser device 10 turns on the flash lamp 12, and then, switches the applied voltage to the Q switch 16 from the second voltage to the first voltage to emit a pulse laser beam. The control means 128 sends a sampling trigger signal to the AD conversion means 122 according to the irradiation of the laser beam, and controls a sampling start timing of the photoacoustic wave.

The control means 128 sends an ultrasonic transmission trigger signal to instruct the transmission control circuit 129 to transmit the ultrasonic wave at the time of the generation of the ultrasound image. If the ultrasonic transmission trigger signal is received, the transmission control circuit 129 allows the ultrasonic wave to be transmitted from the probe 101. The control means 128 sends the sampling trigger signal to the AD conversion means 122 according to the ultrasonic transmission timing, and starts the sampling of the reflected ultrasonic wave.

In the above description, although a case where the probe 101 detects both the photoacoustic wave and the reflected ultrasonic wave in the photoacoustic measurement device 100 has been described, the probe for use in generating the ultrasound image and the probe for use in generating the photoacoustic image may not necessarily be the same. That is, the photoacoustic wave and the reflected ultrasonic wave may be respectively detected by different probes. Furthermore, in the foregoing embodiments, although an example where the laser device constitutes a part of the photoacoustic measurement device has been described, the invention is not limited thereto. The laser device of the invention can be used for a device different from the photoacoustic measurement device.

Although the invention has been described based on the preferred embodiment, the laser device and the photoacoustic measurement device of the invention are not limited to the foregoing embodiments, and various alterations may be carried out from the configurations of the foregoing embodiments and may fall within the scope of the invention.

EXPLANATION OF REFERENCES

10: laser device
11: laser rod
12: flash lamp
13: laser chamber
13a: first portion
13b: second portion
14, 15: mirror
16: Q switch
17: polarizer
18: prism
19: housing
20: shielding lid
21: thin-film portion
22: insulating block
23: insulating member
30: cooling equipment
31, 32: piping
100: photoacoustic measurement device
101: probe
102: ultrasound unit
103: image display means
121: reception circuit
122: AD conversion means
123: reception memory
124: data separation means
125: photoacoustic image generation means
126: ultrasound image generation means
127: image composition means
128: control means
129: transmission control circuit
171: glass plate
172: separation film

What is claimed is:

1. A laser device comprising: a laser rod which includes alexandrite crystal;
an excitation light source which irradiates the laser rod with excitation light; a resonator which includes a pair of mirrors with the laser rod sandwiched therebetween; a Q switch which is inserted into the optical path of the resonator and controls the Q value of the resonator; and a non-coated Brewster polarizer which is inserted at least between the laser rod and the Q switch or between the laser rod and one of the pair of mirrors and selectively transmits light in a predetermined polarization direction among light emitted from the laser rod,
wherein the Q switch includes a Pockels cell, in a case in which an applied voltage to the Pockels cell is a first voltage, the Q value of the resonator is higher than a laser oscillation threshold, and in a case in which the applied voltage is a second voltage higher than the first voltage, the Q value of the resonator is equal to or less than the laser oscillation threshold, and
wherein, in a case in which an input energy to the excitation light source is 20 J, the range of an applied voltage to the Q switch for making the Q value of the resonator equal to or less than the laser oscillation threshold is equal to or greater than 0.5 kV.

2. The laser device according to claim 1,
wherein the optical path of the resonator is sealed within the range of the resonator.

3. The laser device according to claim 1,
wherein at least one of the laser rod or the Q switch has an anti-reflection film at a light incidence end thereof.

4. The laser device according to claim 2,
wherein at least one of the laser rod or the Q switch has an anti-reflection film at a light incidence end thereof.

5. The laser device according to claim 1,
wherein the first voltage is 0 V, and the second voltage is a voltage which makes the Pockels cell function as a quarter-wave plate.

6. The laser device according to claim 1,
wherein the polarizer is constituted of a glass plate disposed at a Brewster angle with respect to the optical axis of light emitted from the laser rod.

7. The laser device according to claim 2,
wherein the polarizer is constituted of a glass plate disposed at a Brewster angle with respect to the optical axis of light emitted from the laser rod.

8. The laser device according to claim 1,
wherein, in a case in which input energy is 20 J, the output energy of laser is equal to or greater than 140 mJ.

9. The laser device according to claim 1,
wherein the polarizer is inserted between the laser rod and the output-side mirror of the pair of mirrors.

10. The laser device according to claim 1,
wherein the polarizers are inserted both between the laser rod and the Q switch and between the laser rod and one of the pair of mirrors.

11. A laser device comprising: a laser rod which includes alexandrite crystal;
an excitation light source which irradiates the laser rod with excitation light; a resonator which includes a pair of mirrors with the laser rod sandwiched therebetween; a Q switch which is inserted into the optical path of the resonator and controls the Q value of the resonator; and
a Brewster polarizer which is inserted at least between the laser rod and the Q switch or between the laser rod and one of the pair of mirrors, selectively transmits light in a predetermined polarization direction among light emitted from the laser rod, and has a film for separating light in the predetermined polarization direction from light in a polarization direction orthogonal to the predetermined polarization direction,
wherein the Q switch includes a Pockets cell, in a case in which an applied voltage to the Pockels cell is a first voltage, the Q value of the resonator is higher than a laser oscillation threshold, and in a case in which the applied voltage is a second voltage higher than the first voltage, the Q value of the resonator is equal to or less than the laser oscillation threshold, and
wherein, in a case in which an input energy to the excitation light source is 20 J, the range of an applied voltage to the Q switch for making the Q value of the resonator equal to or less than the laser oscillation threshold is equal to or greater than 2.5 kV.

12. The laser device according to claim 11,
wherein, in a case in which input energy is 20 J, the output energy of laser is equal to or greater than 140 mJ.

13. A photoacoustic measurement device comprising:
the laser device according to claim 1;
photoacoustic detection unit which detects a photoacoustic wave generated in a subject after the subject is irradiated with a laser beam emitted from the laser device; and
signal processing unit which performs signal processing based on the detected photoacoustic wave.

14. The laser device according to claim 1,
wherein the non-coated Brewster polarizer is a non-coated glass plate of quartz glass or borosilicate glass, disposed at a Brewster angle.

15. The laser device according to claim 1,
wherein the laser rod has a diameter equal to or less than 4 mm, and a rod length of laser rod is equal to or less than 70 mm.

16. The laser device according to claim 11,
wherein the non-coated Brewster polarizer is a non-coated glass plate of quartz glass or borosilicate glass, disposed at a Brewster angle.

17. The laser device according to claim 11,
wherein the laser rod has a diameter equal to or less than 4 mm, and a rod length of laser rod is equal to or less than 70 mm.

* * * * *